United States Patent
Deshpande et al.

(10) Patent No.: US 8,734,345 B2
(45) Date of Patent: May 27, 2014

(54) REAL TIME INTRAVASCULAR MONITORING DEVICE

(75) Inventors: Manish Deshpande, Canton, MA (US); Terri A. Kapur, Sharon, MA (US)

(73) Assignee: Covidien LP, Mansfield, MA (US)

( * ) Notice: Subject to any disclaimer, the term of this patent is extended or adjusted under 35 U.S.C. 154(b) by 282 days.

(21) Appl. No.: 13/195,287

(22) Filed: Aug. 1, 2011

(65) Prior Publication Data
US 2013/0035564 A1 Feb. 7, 2013

(51) Int. Cl.
*A61B 5/00* (2006.01)

(52) U.S. Cl.
USPC .......................................... 600/309; 600/549

(58) Field of Classification Search
USPC ................................. 600/309, 549
See application file for complete search history.

(56) References Cited

U.S. PATENT DOCUMENTS

| | | |
|---|---|---|
| 2007/0191733 A1 | 8/2007 | Gianchandani et al. |
| 2008/0281205 A1 | 11/2008 | Naghavi et al. |
| 2009/0177090 A1 | 7/2009 | Grunwald et al. |
| 2009/0264719 A1 | 10/2009 | Markle et al. |
| 2010/0022944 A1 | 1/2010 | Wilcox |
| 2010/0130836 A1 | 5/2010 | Malchano et al. |
| 2010/0200538 A1 * | 8/2010 | Petisce et al. .................... 216/13 |
| 2010/0280534 A1 | 11/2010 | Sher |
| 2011/0046455 A1 * | 2/2011 | Hengerer et al. ............. 600/309 |

FOREIGN PATENT DOCUMENTS

DE   202 13 708   11/2002

OTHER PUBLICATIONS

European Search Report dated Nov. 30, 2012 in copending European Appln. No. 12178486.

* cited by examiner

*Primary Examiner* — Max Hindenburg
*Assistant Examiner* — Renee Danega
(74) *Attorney, Agent, or Firm* — Thomas M. Johnston, Esq.

(57) ABSTRACT

A real time tissue sampling and analysis system includes a catheter including an elongated body defining at least one internal lumen, a sampling device positionable within the at least one internal lumen of the catheter for collecting a tissue sample, and a biochip disposed within the at least one internal lumen. The biochip includes a substrate for receiving the tissue sample, a marker for interacting with the tissue sample, and a sensor for identifying a characteristic of the tissue sample and transmitting data about the tissue sample to a processing unit for analysis.

7 Claims, 2 Drawing Sheets

REAL TIME INTRAVASCULAR MONITORING DEVICE

TECHNICAL FIELD

The present disclosure relates to intravascular tissue sampling and detection and, more particularly, to catheter assemblies for real time sampling and diagnoses of the morphology of an intravascular clot.

BACKGROUND

Catheters are used for delivering drugs through vasculature and other body lumens for a variety of purposes. It is often desirable to deliver thrombolytic and other substances to the peripheral vasculature, in particular the peripheral venous vasculature, in order to prevent clot formation or to lyse clots in patients suffering from complications, such as thrombosis, or from conditions, such as deep vein thrombosis (DVT).

Typically, however, limited information about clot morphology is available to a clinician prior to selecting a treatment option. Accordingly, treatment methods are chosen in which the probability of clot resolution is high, but not always guaranteed. For example, a clinician may choose to utilize a traditional thrombolytic agent which is not clot specific; however, such agents put the patient at risk as all clotting is inhibited with the use of such drugs. Alternatively, a tissue plasminogen activator (tPA), which is a clot specific thrombolytic, i.e., more effective in the resolution of acute clots than chronic clots, may be utilized. However, utilizing an agent like tPA without knowing the morphology of the clot may result in wasted expense and effort, along with a delay in proper treatment.

While devices are available for measuring the physiological parameters of the vasculature for identifying the presence of blood clots, there is currently no real time detection of clot morphology within the treatment loop. It would be advantageous to provide intravascular devices for sampling and detecting the morphology of a blood clot. Such devices would provide the clinician with information about clot morphology in real time during, or shortly following, tissue sampling, for determining the best course of treatment for breaking up the clot.

SUMMARY

A real time tissue sampling and analysis system in accordance with the present disclosure includes a catheter including an elongated body defining at least one internal lumen, a sampling device positionable within the at least one internal lumen of the catheter for collecting a tissue sample, and a biochip disposed within the at least one internal lumen of the catheter. The biochip includes a substrate for receiving the tissue sample, a marker for interacting with the tissue sample, and a sensor for identifying a characteristic of the tissue sample and transmitting data about the tissue sample to a processing unit for analysis.

The sampling device may be a tissue collecting device such as, for example, scrapers, forceps, tweezers, cutters, vacuums, aspiration needles, syringes, and combinations thereof. In embodiments, the sampling device is positioned on a distal tip of a guidewire.

The marker may be an activator of clot lysis. In such embodiments, the activator may be an anticoagulant or a thrombolytic. In some embodiments, the marker may be a tissue plasminogen activator. The marker may be disposed on the substrate of the biochip. In embodiments, the biochip may include a single marker or an array of markers.

The sensor may be an imaging sensor, a sound sensor, a light sensor, an electrical sensor, an electrochemical sensor, or a combination thereof. In embodiments, the sensor is connected to the processing unit by an electric wire. In other embodiments, the sensor transmits signal to the processing unit via wireless transmission.

In embodiments, the catheter may be a dual or triple lumen catheter.

Methods of determining the morphology of a blood clot in real time are also described. In accordance with an embodiment of the present methods, a vessel containing a blood clot is accessed with a catheter. The catheter includes an elongate body defining at least one internal lumen and a biochip disposed within the at least one lumen. The biochip includes a substrate for receiving a tissue sample, a marker for interacting with the tissue sample, and a sensor for identifying a characteristic of the tissue sample. A tissue sample is obtained from the blood clot and, within the accessed vessel, is subjected to the marker. The response of the tissue sample to the marker is then measured. The tissue sample may be obtained by providing a sampling device within the at least one internal lumen of the catheter.

BRIEF DESCRIPTION OF THE DRAWINGS

Various embodiments of the present disclosure will be described herein with references to the accompanying drawings, wherein.

DETAILED DESCRIPTION OF THE EMBODIMENTS

Various exemplary embodiments of the present disclosure are discussed hereinbelow in terms of medical catheters for vascular access. The catheters are utilized for real time sampling and detection of blood clots, but may also be utilized in the administration and/or withdrawal of fluids to the body of a patient. Such vascular access catheters include, for example, central venous catheters, acute dialysis catheters, chronic dialysis catheters, infusion catheters, and peripheral catheters. It is envisioned that the principles of the present disclosure are equally applicable to a range of catheter applications including surgical, diagnostic, and related treatments of diseases and body ailments of a patient.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician"

should be understood as referring to a doctor, nurse, or other care provider and may include support personnel.

The following discussion includes a description of embodiments of the presently disclosed catheter assembly for real time tissue sampling and analysis, as well as a description of exemplary corresponding methods of use in accordance with the principles of the present disclosure.

Figure 1A:
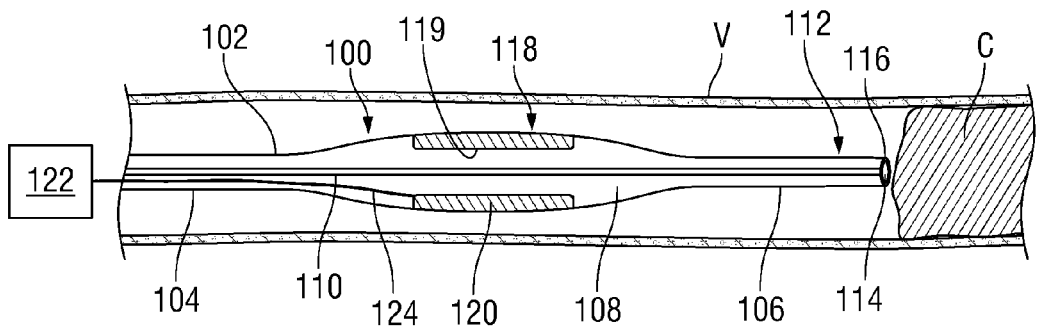
FIGS. 1A and 1B are perspective, cross-sectional views of a real time tissue sampling and analysis system in accordance with one embodiment of the present disclosure.
Figure 1B:
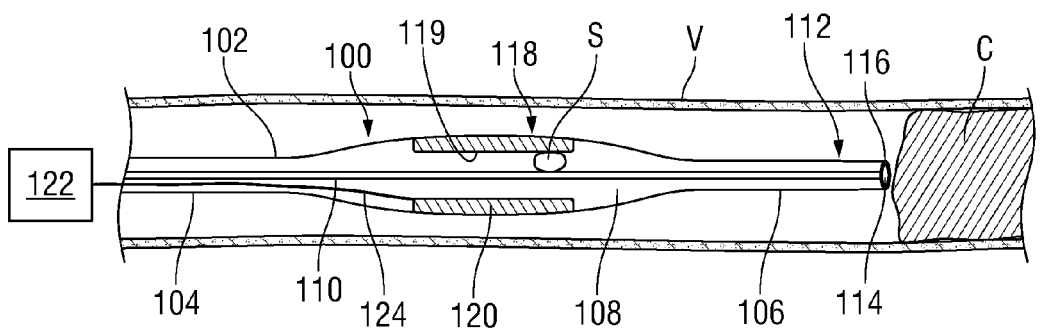

Referring now to the figures, wherein like components are designated by like reference numerals throughout the several views, FIGS. 1A and 1B illustrate one embodiment of a catheter assembly for use in real time sampling and diagnoses of a blood clot. Catheter 100 includes an elongate tubular body 102 having a proximal region 104 and a distal region 106. The elongate tubular body 102 of catheter 100 defines an internal lumen 108 that is configured and dimensioned to slidably receive a guidewire 110 and/or sampling device 114, as well as to allow for the passage of fluids therethrough.

Sampling device 114 is utilized to extract a small sample "S" of tissue, e.g., blood clot "C". Sampling device 114 may be any tissue collecting device such as scrapers, forceps, tweezers, cutters, among other mechanical tissue collection tools within the purview of those skilled in the art. As illustrated in the current embodiment, the guidewire 110 includes a wire head 112 that includes a sampling device 114 at the tip 116 thereof for extracting the tissue sample "S". Alternatively, or in addition to mechanical tissue collection tools, sampling device 114 may include suction means (not shown), such as an aspiration needle, syringe, or other vacuum source, which may be attached to the proximal region 104 of the elongate tubular body 102 to aspirate or draw the tissue sample "S" through internal lumen 108 proximally towards biochip 118, as illustrated in FIG. 1B. The tissue sample "S" may then be processed by biochip 118.

Biochip 118 is intended for carrying out an assay designed to determine the chemical composition of a clot (for example, to identify the age of the clot and to discriminate between acute and chronic clots), to establish the biochemical composition of the clot, to gauge the response of the clot to a specific treatment modality, as well as to test other parameters of interest. The biochip 118 includes at least one probe or marker 119 disposed on, or adhered to, a surface of a substrate thereof for contacting and reacting with the tissue sample "S". The surface chemistry provided by marker 119 binds with target molecules in the tissue sample "S". Alternatively, the biochip 118 may include a substrate on which the tissue sample "S" may be attached. In such embodiments, a solution containing a marker of interest may then be introduced into the internal lumen 108 of the catheter 100 for reaction with the tissue sample "S".

In embodiments, the marker 119 utilized with the biochip 118 may be an activator of clot lysis. Such activators include, for example, anticoagulants such as heparin and warfarin; thrombolytics such as tissue plasminogen activator (tPA), urokinase, and streptokinase; and other active agents for lysing and/or macerating a blood clot as is within the purview of those skilled in the art. The marker 119, however, may be any marker conducive to determining the chemical composition of the blood clot, such as proteins, enzymes, peptides, other molecular or biological materials, analytes, or reagents, that is measurable during clot lysis. The marker 119 may be reactive to by-products produced by the tissue sample "S" thereby exhibiting a measurable increase or decrease in the level of the marker 119, the marker 119 may produce a visual change in the composition of the tissue sample "S", or indicate the presence of a specific substance in the tissue.

In embodiments, biochip 118 may include a multi-probe assay for testing an array of markers 119 to analyze the fibrinolysis of a tissue sample "S". For example, biochip 118 may include two or more activators of clot lysis, separately disposed on biochip 118. The multiple assay approach improves the efficiency of testing a blood clot, and may save time and treatment costs. In some embodiments, the tissue sample may be tested in replicates, such as duplicate or triplicate.

Biochip 118 also includes an integrated sensor 120 for sensing properties of, or changes to, the tissue sample "S" resulting from the interaction of the sample "S" with the marker 119 in real time in order to detect a characteristic of the tissue sample "S".

Sensor 120 may be an image sensor such as a CCD or CMOS image sensor; a sound sensor such as ultrasound; a light sensor such as a photodiode; or other electrical or electrochemical sensor for measuring characteristics such as resistivity, impedance, temperature, pH, enzymatic activity, etc. of the tissue sample "S". Other suitable sensors 120 for use with the catheter assembly of the present disclosure include, for example, microoptical detectors for detection of particle size, electrochemical detectors, acoustic or electrical sensors to evaluate tissue stiffness, sensors to detect hemoglobin content or other sensors that would be sensitive to the morphology of the tissue being evaluated.

Figure 4A:
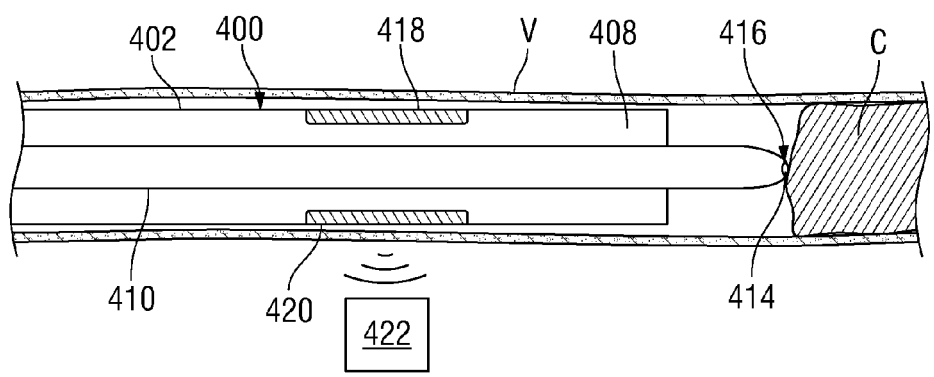
FIGS. 4A and 4B are perspective, cross-sectional views of a real time tissue sampling and analysis system in accordance with another embodiment of the present disclosure.
Figure 4B:
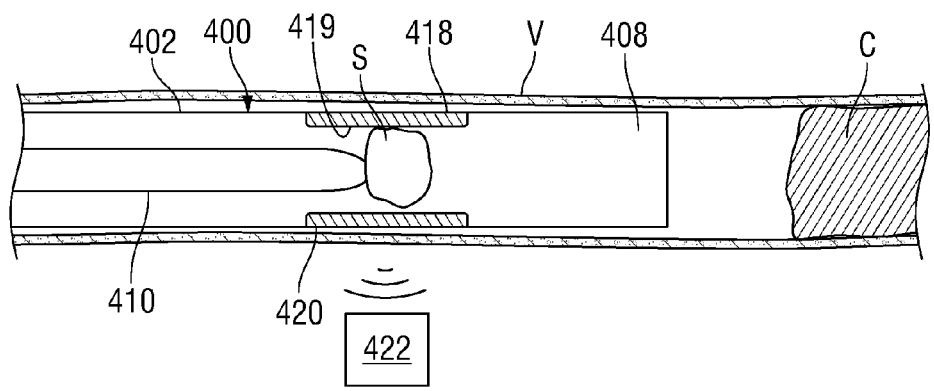

The signals captured by the sensor 120 may be transmitted to a processing unit 122 via electric wires 124 for analysis by a clinician. Alternatively, sensor 120 may be connected to a wireless receiver (FIGS. 4A-4B). The data acquisition may be continuous or may be intermittent, with readings taken at pre-determined time intervals. The signals produced contain information about a specific characteristic of the tissue sample "S", which in turn imparts information about the morphology of the blood clot "C" which can be utilized in determining a proper course of treatment for successfully breaking up the clot.

While biochip 118 is illustrated as being positioned within a substantially central portion of the internal lumen 108 of catheter 100, the biochip 118 may be of any length and size, and maintained on any portion of the elongate tubular body 102 of the catheter 100. In embodiments, biochip 118 may be positioned off-set from the center towards, or on, either proximal or distal regions 104, 106 of catheter 100. Catheter 100 may also include more than one biochip 118 positioned within internal lumen 108 for measuring different properties of the tissue sample "S". In other embodiments, a microarray of markers 119 and/or sensors 120 may be utilized on a single biochip 118.

While catheter 100 is illustrated as including a single internal lumen 108, other catheter configurations are envisioned. It should be appreciated that the principles of the present disclosure are equally applicable to catheters having alternative tip configurations, such as staggered tip or split-tip designs, catheters including a single lumen or multiple lumens such as dual and triple lumen catheters, and other catheters of various cross-sectional geometries, and/or catheters that are employable in a variety of other medical procedures. Suitable non-exclusive examples of catheters falling within the scope of the present disclosure include, for example, the PALINDROME™ and MAHURKAR® Maxid™ catheters, each of which is made available by Covidien, which maintains a principal place of business at 15 Hampshire Street, Mansfield, Mass.

Figure 2:
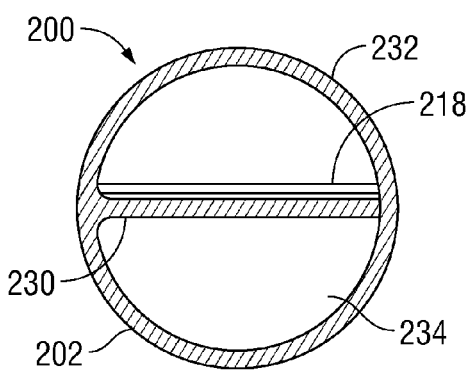
FIG. 2 is an end view of a dual lumen catheter which may be utilized with the real time tissue sampling and analysis system of the present disclosure.
Figure 3:
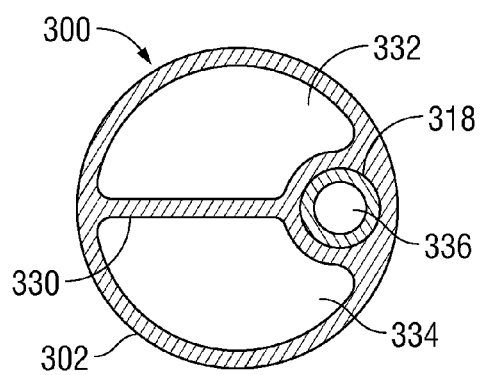
FIG. 3 is an end view of a triple lumen catheter which may be utilized with the real time tissue sampling and analysis system of the present disclosure.

For example, as illustrated in FIG. 2, catheter 200 includes tubular body 202 containing a septum 230 dividing the tubular body 202 into first and second lumens 232, 234. First lumen 234 includes biochip 218 with integrated sensor 220 for sensing and capturing data, as discussed above with reference to FIGS. 1A and 1B. Similarly, FIG. 3 illustrates a catheter 300 including a tubular body 302 divided into first and second lumens 332, 334 via septum 330. Septum 330 is bifurcated at an end thereof to form a third lumen 336. Third lumen 336 includes biochip 318, however, it is envisioned that biochip 318 may be positioned in any of the lumens of a multi-lumen catheter. Additionally, a tissue sampling device (FIGS. 1A-1B) may be introduced through any lumen of a multi-lumen catheter.

Referring now to FIGS. 4A and 4B, a catheter assembly in accordance with another embodiment of the present disclosure is provided. It should be understood that the catheter assembly of FIGS. 4A-4B is similar to the catheter assembly of FIGS. 1A-1B and therefore will only be described with respect to the differences therebetween. Catheter 400 includes an elongate tubular body 402 defining an internal lumen 408. Guidewire 410 includes a sampling device 414 at a tip 416 thereof for extracting a small sample "S" of a blood clot "C". After sample collection, guidewire 410 is manually retracted so that tissue sample "S" is positioned proximate to biochip 418, as illustrated in FIG. 4B. The tissue sample "S" may then be prepared and processed by a biochip 418 within internal lumen 408 of catheter 400.

Methods of utilizing the real time sampling and detecting systems of the present disclosure are also described. In one embodiment, the method may include accessing a vessel, collecting a tissue sample from a blood clot, analyzing the tissue sample, and treating the clot.

Initially, a target vessel "V" containing the blood clot "C" must be accessed. Various techniques may be employed for the insertion of catheters into the body including, but not limited to, the use of guidewires, introduction stylets or obturators, dilator/sheath assemblies, and the like. For example, during such procedures, a hollow needle cannula may be inserted into a target vessel in, for example, the venous system, to create a venotomy (entry) site. Upon positioning the needle cannula within the target vessel, a guidewire is inserted through a proximal end of the needle cannula, into the target vessel, and advanced to a desired location within the target vessel proximate to the blood clot. The needle cannula is then withdrawn, leaving a distal end of the guidewire positioned within the target vessel at the desired location, and a proximal end of the guidewire extending outwardly from the venotomy site. A dilator/sheath assembly may then be threaded over the guidewire and into the vessel through the venotomy site to expand the venotomy site and target vessel to facilitate insertion of a catheter.

With reference again to FIGS. 1A and 1B, the guidewire 110 may be positioned proximate to blood clot "C" (FIG. 1A), whereby sampling device 114 may be utilized to collect a tissue sample "S" from the blood clot "C". The tissue sample "S" is then aspirated into internal lumen 108 to biochip 118 (FIG. 1B). In other embodiments, rather than aspirate the tissue sample "S" towards the biochip 118, the tissue sample "S" may be manually positioned proximate to biochip 418 by drawing the guidewire 410 proximally, as illustrated in FIGS. 4A-4B. Biochip 118 includes a marker 119 on a surface thereof, for example, tPA. Alternatively, tissue sample "S" may be exposed to a marker 119, such as tPA, by introducing the thrombolytic into lumen 108 of catheter 100. The exposure of the tissue sample "S" to tPA will enable a clinician to determine if the clot is acute or chronic. Sensor 120 measures properties of, and/or changes in, the tissue sample "S", such as by an image processing or ultrasound sensor, and the signals are transmitted to the processing unit 122 for analysis by a clinician. The tissue sample "S" should be exposed to tPA for a sufficient length of time to determine if clot lysis has occurred. Thus, the sensor 120 may monitor for the existence of debris, such as by monitoring a change in the viscosity, density, or size of the tissue sample "S", in real time. If the tPA is able to break up the tissue sample "S", the clot "C" can be considered acute and the guidewire 110 and/or catheter 100 can be retracted from vessel "V".

Thereafter, a course of treatment can be selected, such as the use of a TRELLIS™ Peripheral Infusion System available through Covidien, for removal of an acute clot. On the other hand, if the tPA has little to no effect on the tissue sample, the blood clot may be considered chronic and alternative treatment approaches may be sought, such as the use of blood clot therapy products available through ev3 Endovascular, Inc., Plymouth, Minn.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the system based on the above-described embodiments. Accordingly, the present disclosure is not to be limited by what has been particularly shown and described, except as indicated by the appended claims.

What is claimed is:

1. A method for determining the morphology of a blood clot in real time, the method comprising:
    accessing a vessel containing a blood clot with a catheter, the catheter including an elongate body defining at least one internal lumen and a biochip disposed within the at least one lumen, the biochip including a substrate for receiving a tissue sample, a marker for interacting with the tissue sample, and a sensor for identifying a characteristic of the tissue sample;
    obtaining a tissue sample from the blood clot;
    subjecting the tissue sample, within the accessed vessel, to the marker; and
    measuring the response of the tissue sample to the marker.

2. The method of claim 1, wherein the step of obtaining a tissue sample further includes the step of providing a sampling device within the at least one internal lumen of the catheter.

3. The method of claim 1, wherein the step of obtaining a tissue sample further includes the step of extracting the tissue sample with a sampling device positioned within the at least one internal lumen of the catheter, the sampling device selected from the group consisting of scrapers, forceps, tweezers, and cutters.

4. The method of claim 3, wherein the step of extracting the tissue sample further includes the step of positioning the sampling device proximate to the blood clot.

5. The method of claim 4, wherein the step of subjecting the tissue sample further includes the step of retracting the sampling device proximally within the at least one internal lumen of the catheter so that the tissue sample is positioned proximate to the biochip.

6. The method of claim 1, wherein the step of obtaining a tissue sample further includes the step of aspirating the tissue sample into the at least one internal lumen proximally towards the biochip with one of an aspiration needle, a syringe, and a vacuum.

7. The method of claim 1, further comprising the step of treating the blood clot.

\* \* \* \* \*